(12) United States Patent
de Boer et al.

(10) Patent No.: US 7,202,238 B2
(45) Date of Patent: Apr. 10, 2007

(54) DIAZABICYCLO ALKANE DERIVATIVES WITH NK$_1$ ANTAGONISTIC ACTIVITY

(75) Inventors: Dirk de Boer, Weesp (NL); Hein K. A. C. Coolen, Weesp (NL); Mayke B. Hesselink, Weesp (NL); Wouter I. Iwema Bakker, Weesp (NL); Gijsbert D. Kuil, Weesp (NL); Jan H. van Maarseveen, Weesp (NL); Andrew C. McCreary, Weesp (NL); Gustaaf J. M. van Scharrenburg, Weesp (NL)

(73) Assignee: Solvay Pharmaceuticals B.V. (NL)

( * ) Notice: Subject to any disclaimer, the term of this patent is extended or adjusted under 35 U.S.C. 154(b) by 298 days.

(21) Appl. No.: 10/490,364

(22) PCT Filed: Apr. 2, 2003

(86) PCT No.: PCT/EP03/50086

§ 371 (c)(1),
(2), (4) Date: Mar. 22, 2004

(87) PCT Pub. No.: WO03/084955

PCT Pub. Date: Oct. 16, 2003

(65) Prior Publication Data

US 2005/0119267 A1 Jun. 2, 2005

(30) Foreign Application Priority Data

Apr. 4, 2002 (EP) .................. 02076405

(51) Int. Cl.
| | |
|---|---|
| A01N 43/00 | (2006.01) |
| A01N 43/58 | (2006.01) |
| A01N 43/50 | (2006.01) |
| A61K 31/55 | (2006.01) |
| C07D 241/36 | (2006.01) |

(52) U.S. Cl. .................. 514/214.02; 514/249; 540/579; 540/580; 544/349

(58) Field of Classification Search .................. None
See application file for complete search history.

(56) References Cited

U.S. PATENT DOCUMENTS 6,284,757 B1 * 9/2001 Sanner ................... 514/249

FOREIGN PATENT DOCUMENTS

| EP | 0 655 442 A1 | 5/1995 |
|---|---|---|
| EP | 0 899 270 A1 | 3/1999 |
| EP | 1 176 144 A1 | 1/2002 |
| GB | 1125112 | * 8/1968 |
| WO | WO 96/37488 | 11/1996 |
| WO | WO 96/37489 | 11/1996 |
| WO | WO 97/22597 | 6/1997 |
| WO | WO 98/57954 | 12/1998 |
| WO | WO 00/35915 | 6/2000 |

OTHER PUBLICATIONS

Humphrey, J.M. "Medicinal Chemistry of Selective Neurokinin-1 Antagonists" Current Topics in Medicinal Chemistry, vol. 3(12), pp. 1423-1435 (2003).*
Adamczeski, M. et al., "Novel Sponge-Derived Amino Acids. 5.[1] Structures, Stereochemistry, and Synthesis of Several New Heterocycles", Journal of the American Chemical Society, vol. 111, No. 2, pp. 647-654, (1989).
Shigemori, H. et al., "Three New Metabolites from the Marine Yeast *Aureobasidium Pullulans*", Journal of Natural Products, vol. 61, No. 5, pp. 696-698, (1998).

* cited by examiner

*Primary Examiner*—Zachary C. Tucker
(74) *Attorney, Agent, or Firm*—Finnegan, Henderson, Farabow, Garrett & Dunner, L.L.P.

(57) ABSTRACT

The present invention relates to a group of unique diazabicyclo alkane derivatives having interesting neurokinin-NK$_1$ receptor antagonistic activity represented by the general formula (1) wherein: $R^1$ represents phenyl, 2-indolyl, 3-indolyl, 3-indazolyl or benzo[b]thiophen-3-yl, which groups may be substituted with halogen or alkyl (1–3C), $R^2$ and $R^3$ independently represent halogen, H, OCH$_3$, CH$_3$ and CF$_3$, $R^4$, $R^5$ and $R^6$ independently represent H, OH, O-alkyl (1–4C), CH$_2$OH, NH$_2$, dialkyl(1–3C)N, pyrrolidin-1-yl, piperidin-1-yl, morpholin-4-yl or morpholin-4-yl substituted with one or two methyl or methoxymethyl groups, morpholin-4-ylamino, morpholin-4-ylmethyl, imidazol-1-yl, thiomorpholin-4-yl, 1,1-dioxothiomorpholin-4-yl or 3-oxa-8-azabicyclo[3.2.1]oct-8-yl; $R^4$ and $R^5$ together may represent a keto, a 1,3-dioxan-2-yl or a 1,3-dioxolan-2-yl group, X represents either O or S, n has the value of 1, 2 or 3, a is the asymmetrical carbon atom 8a, 9a or 10a when n equals 1, 2 or 3 respectively The invention also relates to a method for the preparation of the novel compounds, and to pharmaceutical compositions containing at least one of these compounds as an active ingredient (1)

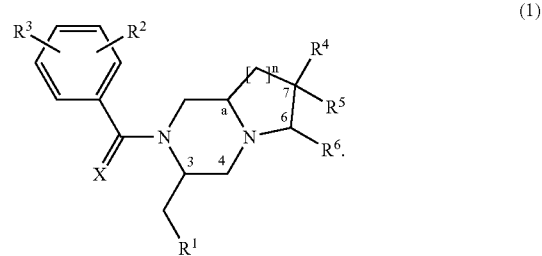

6 Claims, No Drawings

DIAZABICYCLO ALKANE DERIVATIVES WITH NK₁ ANTAGONISTIC ACTIVITY

CROSS REFERENCE TO RELATED APPLICATION

This application claims the benefit under 35 U.S.C. 371 of PCT/EP03/50086 filed Apr. 2, 2003, the content of which is incorporated herein by reference in full.

The present invention relates to a group of unique diazabicyclo alkane derivatives having interesting neurokinin-$NK_1$ receptor antagonistic activity.

The invention also relates to a method for the preparation of the novel compounds, and to pharmaceutical compositions containing a pharmacologically active amount of at least one of these compounds as an active ingredient.

From the European patent application EP 0655442 piperazine derivatives with neurokinin antagonistic activity are known. Novel piperazine derivatives sharing this biological activity were disclosed in EP 0899270 which describes a series of 2-(3-indolylmethyl)-1-benzoyl-4-[(2-(benzylamino)ethyl)aminocarbonyl)]piperazine derivatives having $NK_1$ antagonistic activity.

Surprisingly, it has now been found that piperazine derivatives are also $NK_1$ antagonists when the piperazine ring and it's N-4 substituent are fused to yield 1,4-diazabicyclo[4.3.0]nonane, 1,4-diazabicyclo[4.4.0]decane or 1,4-diazabicyclo[4.5.0]undecane derivatives.

The invention relates to compounds of the general formula (1)

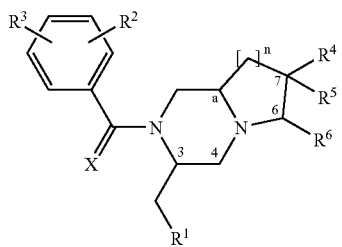

(1)

wherein:
$R^1$ represents phenyl, 2-indolyl, 3-indolyl, 3-indazolyl or benzo[b]thiophen-3-yl, which groups may be substituted with halogen or alkyl (1–3C),
$R^2$ and $R^3$ independently represent halogen, H, $OCH_3$, $CH_3$ and $CF_3$,
$R^4$, $R^5$ and $R^6$ independently represent H, OH, O-alkyl (1–4C), $CH_2OH$, $NH_2$, dialkyl(1–3C)N, pyrrolidin-1-yl, piperidin-1-yl, morpholin-4-yl or morpholin-4-yl substituted with one or two methyl or methoxymethyl groups, morpholin-4-ylamino, morpholin-4-ylmethyl, imidazol-1-yl, thiomorpholin-4-yl, 1,1-dioxothiomorpholin-4-yl or 3-oxa-8-azabicyclo[3.2.1]oct-8-yl; $R^4$ and $R^5$ together may represent a keto, a 1,3-dioxan-2-yl or a 1,3-dioxolan-2-yl group,
X represents either O or S,
n has the value of 1, 2 or 3,
a is the asymmetrical carbon atom 8a, 9a or 10a when n equals 1, 2 or 3 respectively, and pharmacologically acceptable salts thereof.

All compounds having formula (1) in which the substituents on the asymmetrical carbon atoms 3 and 'a', as well as on the potentially asymmetrical carbon atoms 6 and 7, are in either the R-configuration or the S-configuration belong to the invention.

Also prodrugs, i.e. compounds which when administered to humans by any known route, are metabolised to compounds having formula (1), belong to the invention. In particular this relates to compounds in which $R^4$, $R^5$ or $R^6$ represent a hydroxy or hydroxymethyl-group, a typical example being 3,5-bis(trifluoromethyl)phenyl-[6-hydroxymethyl-3-(1H-indol-3-ylmethyl)-hexahydropyrrolo[1,2-a]pyrazin-2-yl]-methanone (compound 1 and it's enantiomers, see below). Such compounds can be esterified to yield compounds which can be metabolized to compounds having formula (1).

The invention particularly relates to compounds having formula (1) wherein $R^1$ is 3-indolyl, $R^2$ and $R^3$ are $CF_3$ groups in the 3 and 5 positions, X represents a keto group, n has the value of either 1 or 2, and 'a', $R^4$, $R^5$ and $R^6$ have the meanings given above, and including all possible stereoisomers as outlined above.

Even more preferred are compounds of the invention as described above, wherein $R^4$ or $R^6$ represents or contains either a morpholino or a hydroxymethyl group, $R^5$ is hydrogen and which stereochemistry is 3R The compounds having formula (1) and their salts can be obtained according to at least one of the following methods known for compounds of this type.

The compounds of the present invention in which n=1 and $R^4$ and $R^5$ are hydrogen may be prepared by the general route outlined in Scheme 1.

Scheme 1

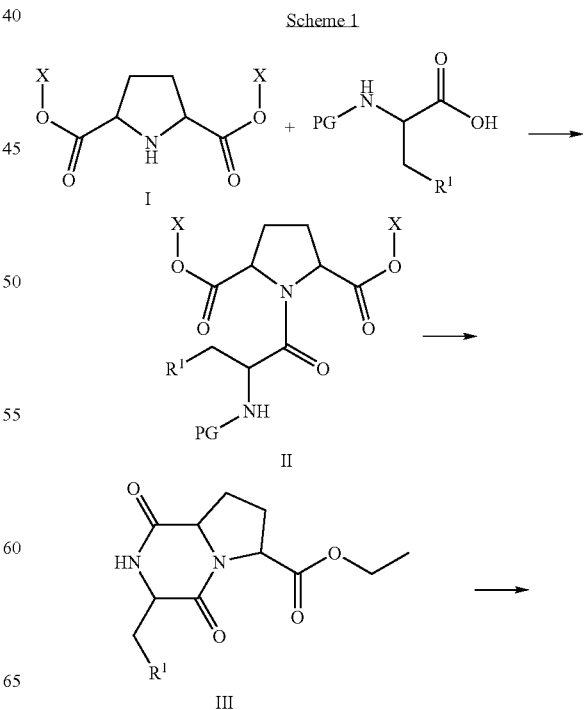

-continued

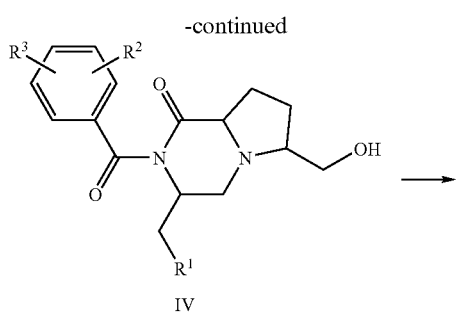

IV

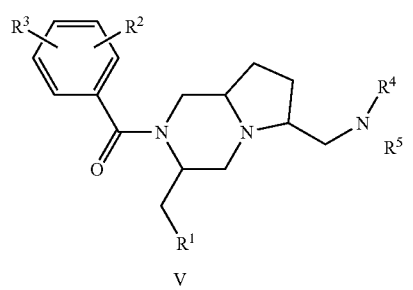

V

Thus the dicarboxylic acid diester I (prepared analogously to the method of G. Cignnarella, G. Nathansohn *J. Org. Chem.,* 1961, 26, 1500) can be coupled to an appropriately protected amino acid under standard peptide coupling procedures as described in M. Bodanszky, A. Bodanszky *The Practice of Peptide Synthesis*, Springer-Verlag, 1994; ISBN: 0-387-57505-7, to afford amide II. The protective group in II (given in formula II as 'PG') can be removed using known procedures (T. W. Greene, P. G. M. Wuts *Protective groups in organic synthesis,* 3$^{rd}$ ed., John Wiley & Sons, 1999). Subsequent cyclisation gives the substituted diketopiperazine III, use of a chiral amino acid would result in the formation of diastereomers and these can be separated at this stage using standard chromatographic methods. Reduction of III with an active hydride reagent such as lithium aluminum hydride leads to an amino alcohol, which can be acylated with an appropriate acid chloride, under conditions that are generally known in the art, to afford IV. Conversion of the alcohol to an appropriate leaving group, such as a methanesulfonate, and subsequent reaction with an amine affords compounds V. Details of compounds synthesized by this route are given in example 1, below.

Ester prodrugs of compounds IV could be obtained by acylation with acid chlorides in a solvent such as acetonitrile in the presence of a base such as diisopropylethylamine, at temperatures between 20° C. and 80° C. (see example 6, below).

The compounds of the invention in which n=1 and R$^6$=H may be prepared by the general route outlined in Scheme 2. Thus reaction of an amino acid ester with an appropriately protected 4-hydroxyproline derivative under standard peptide coupling procedures as described in M. Bodanszky, A. Bodanszky *The Practice of Peptide Synthesis*, Springer-Verlag, 1994; ISBN: 0-387-57505-7 afforded dipeptide VI. The protective group in VI can be removed using known procedures (T. W. Greene, P. G. M. Wuts *Protective Groups in Organic Synthesis,* 3$^{rd}$ ed., John Wiley & Sons, 1999). Subsequent cyclisation affords the substituted diketopiperazine VII, this reaction may be realized by stirring in a mixture of acetonitrile and piperidine. Protection of the hydroxygroup of VII as a silyl ether, by standard methods such as those described in T. W. Greene, P. G. M. Wuts *Protective Groups in Organic Synthesis*, John Wiley & Sons, 1999, and subsequent reduction with an active hydride reagent such as lithium aluminum hydride leads to amino alcohols like VIII. Compounds of formula VIII can be acylated with an appropriate acid chloride, under standard conditions, to afford IX. Conversion of the alcohol to an appropriate leaving group, such as a methanesulfonate, and subsequent reaction with an amine affords compounds X. Details of compounds synthesized by this route are given in example 2, below.

Scheme 2

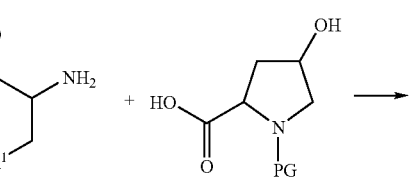

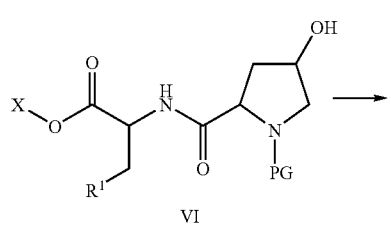

VI

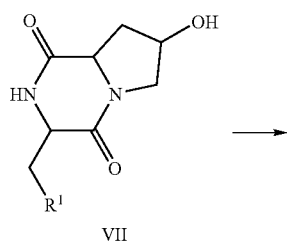

VII

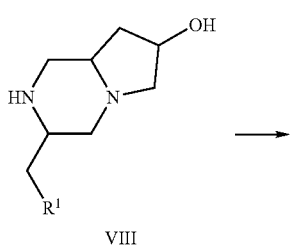

VIII

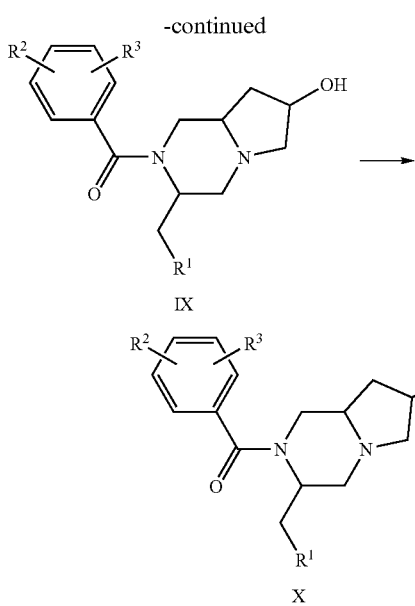

The compounds of the present invention in which n=2 and $R^6$=H may be prepared by the general route outlined in Scheme 3. Thus reaction of an amino acid ester with 5-oxo-piperidine-1,2-dicarboxylic acid 1-benzyl ester (H. C. Beyerman, P. Boekee *Recl. Trav. Chim. Pays-Bas,* 1959, 78, 648) under standard peptide coupling procedures as described in M. Bodanszky, A. Bodanszky *The Practice of Peptide Synthesis*, Springer-Verlag, 1994; ISBN: 0-387-57505-7 afforded dipeptides XI, use of a chiral amino acid would result in the formation of diastereomers and these can be separated at this (or a later) stage using standard chromatographic methods. Protection of the ketone in XI as a cyclic or acyclic ketal, such as those described in T. W. Greene, P. G. M. Wuts *Protective Groups in Organic Synthesis*, John Wiley & Sons, 1999, yields compounds of formula XII, in which A and B represent a cyclic or acyclic ketal. This reaction can be conducted following conventional methods that are generally known in the art. Removal of the benzyloxycarbonyl group under reductive conditions ($H_2$, Pd/C) in a solvent such as methanol, followed by acid catalyzed cyclisation afforded diketopiperazines of formula XIII. Reduction of XIII with an active hydride reagent such as lithium aluminum hydride leads to an amine, which can be acylated with an appropriate acid chloride, under conditions that are generally known in the art, to afford XIV. Hydrolysis of the ketal to form XV can be done by methods as described in T. W. Greene, P. G. M. Wuts *Protective Groups in Organic Synthesis*, John Wiley & Sons, 1999. Reductive amination of XV with a suitable amine, in a solvent such as 1,2-dichloroethane, with a reducing agent such as sodium triacetoxyborohydride, affords compounds of the formula XVI.

Alternatively XVI can be prepared from XV by reduction of the ketone with a reducing agent such as sodium triacetoxyborohydride in a solvent such as acetic acid to the alcohol XVII. The alcohol can be transformed into a leaving group (L) such as chloro, bromo, or methanesulfonate, under conditions generally known in the art, to give XVIII. Substitution of the leaving group in XVIII with a suitable amine, in a solvent such as acetonitrile affords compounds of formula XVI. Details of compounds synthesized by this route are given in examples 3, 4 and 5, below.

Scheme 3

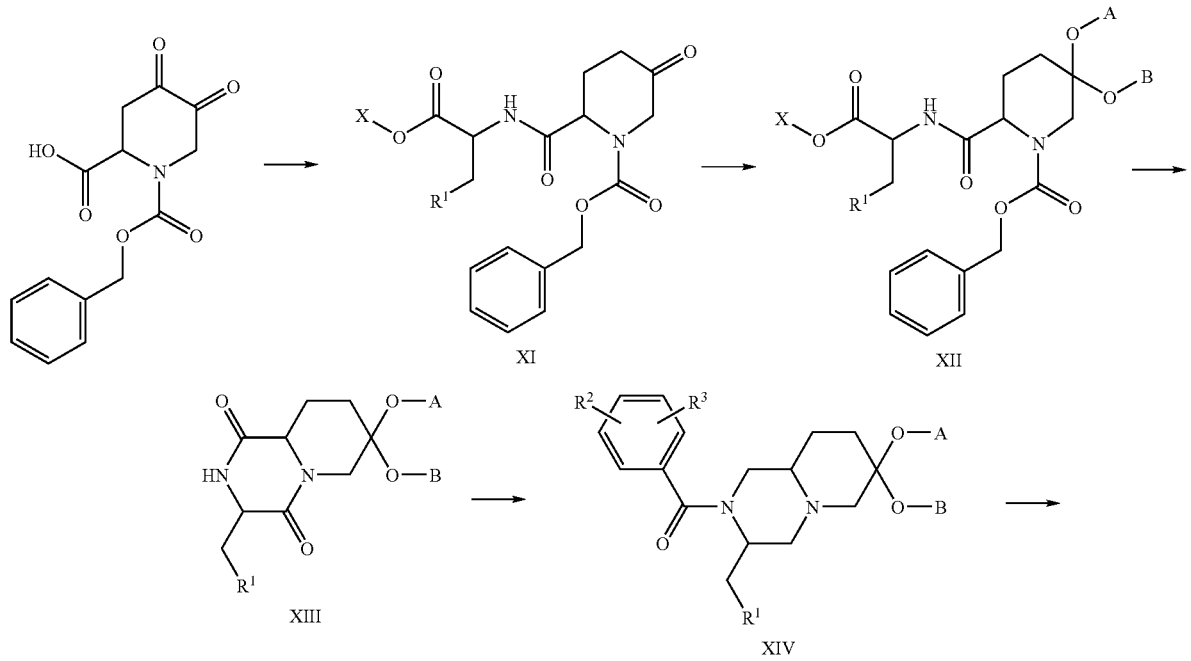

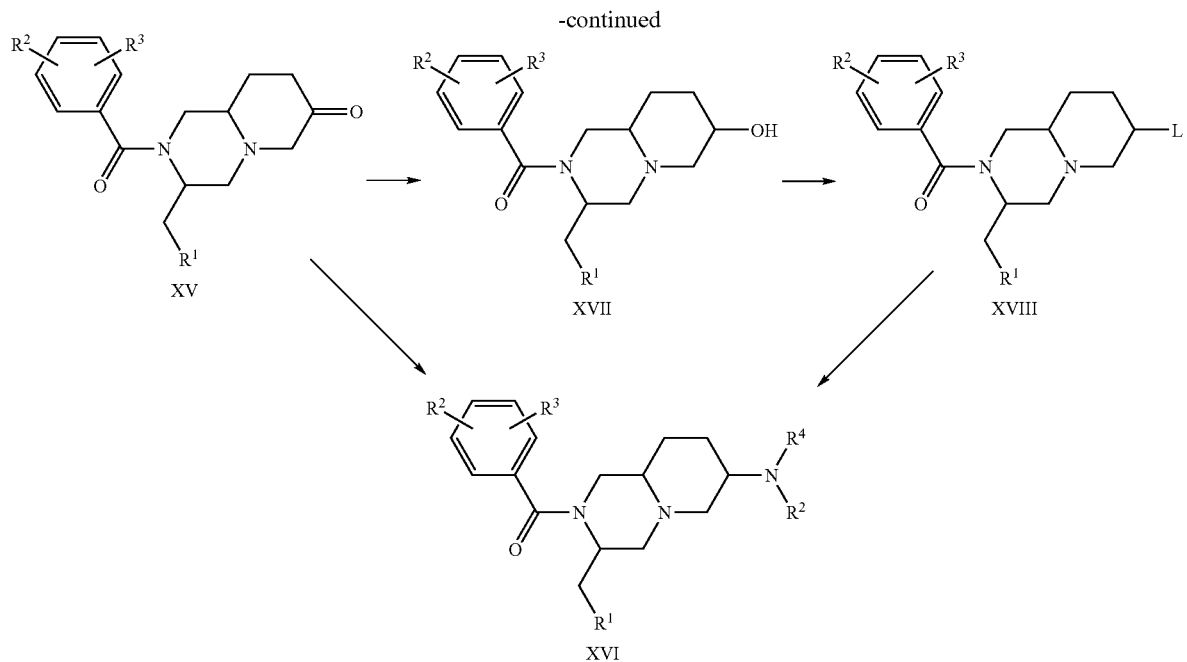

Intermediates VIII (scheme 2), XIII (scheme 3) and XVIII (scheme 3) are novel compounds. The invention also relates to these novel compounds.

Suitable acid addition salts can be formed with inorganic acids such as hydrochloric acid, sulphuric acid, phosphoric acid and nitric acid, or with organic acids such as citric acid, fumaric acid, maleic acid, tartaric acid, acetic acid, trifluoro acetic acid, benzoic acid, p-toluene sulphonic acid, methanesulphonic acid and naphthalene sulphonic acid.

The compounds of the invention of the general formula (1), as well as the salts thereof, have $NK_1$ antagonistic activity and show a good bioavailability. They are useful in the treatment of disorders in which neurokinins which interact with $NK_1$ receptors, e.g. neurokinin-1 (=Substance P) are involved, or that can be treated via manipulation of those systems. For instance in acute and chronic pain, emesis, inflammatory diseases such as meningitis, arthritis, asthma, psoriasis and (sun)burns; gastro-intestinal disorders, in particular irritable bowel syndrome, inflammatory bowel disease (Crohn's disease), ulcerative colitis; bladder or GI tract hypermotility disorders, urinary tract inflammation; allergic responses such as eczema and rhinitis; cardiovascular disorders such as hypertension, atherosclerosis, edema, angina, cluster headache and migraine; cutaneous diseases such as urticaria, lupus erythematosus and pruritus; respiratory disorders including chronic obstructive pulmonary disease, bronchospams, bronchopneumonia, bronchitis, respiratory distress syndrome and cystic fibrosis; various neoplastic diseases; psychiatric and/or neurological disorders such as schizophrenia and other psychotic disorders; mood disorders such as bipolar I disorders, bipolar II disorders and unipolar depressive disorders like minor depression, seasonal affective disorder, postnatal depression dysthymia and major depression; anxiety disorders including panic disorder (with or without agoraphobia), social phobia, obsessive compulsive disorder (with or without co-morbid chronic tic or schizotypal disorder), posttraumatic stress disorder and generalized anxiety disorder; substance related disorders, including substance use disorders (like dependence and abuse) and substance induced disorders (like substance withdrawal); pervasive development disorders including autistic disorder and Rett's disorder; attention deficit and disruptive behavior disorders such as attention deficit hyperactivity disorder; impulse control disorders like agression, pathological gambling; eating disorders like anorexia nervosa and bulimia nervosa, obesity; sleep disorders like insomnia; tic disorders like Tourette's disorder; restless legs syndrome; disorders characterized by impairment of cognition and memory such as Alzheimer's disease, Creutzfeldt-Jacob disease, Huntington's disease, Parkinson's disease and neurorehabilitation (post-traumatic brain lesions)

The NK1 antagonistic properties of the compounds of the invention were tested using the methods outlined below.

Pharmacological Methods

Receptor Binding for Human $NK_1$ Receptors

Affinity of the compounds for human $NK_1$ receptors was assessed using radio-receptor binding assays. Membrane preparations were prepared from Chinese Hamster Ovarium fibroblast (CHO) cells in which the human $NK_1$ receptor was stably expressed. Membranes were incubated with [$^3$H]-substance P in the absence or the presence of specified concentrations of the compounds, diluted in a suitable buffer in presence of peptidase inhibitor for 10 min at 25° C. Separation of bound radioactivity from free was done by filtration over Whatman GF/B glass fiber filters with two 5 sec washings. Bound radioactivity was counted by liquid scintillation counting using a Betaplate counter. Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_i$ values were calculated by correcting the $IC_{50}$ values for radioligand concentration and its affinity for the human $NK_1$ receptor according to the Cheng-Prusoff equation:

$$pK_i=-\log [IC_{50}/(1+S/K_d)]$$

in which the $IC_{50}$ is as described above, S is the concentration [$^3$H]-substance P used in the assay expressed in mol/l, and $K_d$ is the equilibrium dissociation constant of [$^3$H]-substance P for human $NK_1$ receptors (in mol/l).

cAMP Measurements

The effects of test compounds at formation of cyclic AMP (cAMP) was assessed using CHO fibroblast cells, stably expressing cloned human $NK_1$ receptors. In addition to coupling to phospholipase C, human $NK_1$ receptors are also able to stimulate adenylate cyclase, which converts ATP into cAMP. For tests, cells were cultured in 24-well plates. Prior to experiments, medium was replaced by serum-free α-DMEM culture medium, containing [$^3$H]-adenine which is taken up by the cells and converted sequentially into radiolabeled adenosine, AMP, ADP and ultimately into radiolabeled ATP. After 2 hrs, cells were rinsed twice with phosphate-buffered saline (pH 7.4) in presence of 1 mM isobutylmethylxanthine (IBMX; inhibitor of phosphodi-esterases that hydrolyse cAMP into AMP). Subsequently, cells were stimulated by 10 nM substance P in absence or presence of test compounds in appropriate dilutions in PBS/IBMX for 20 min. After stimulation, medium was aspirated and cells were extracted by 5% trichloroacetic acid. Radiolabeled ATP and cAMP were recovered from the extracts using sequential column chromatography. Extracts were separated by ion-exchange chromatography over DOWEX 50WX4 columns, allowing the recovery of ATP. Columns were subsequently put on top of aluminum oxide columns and eluted with water. Recovery of cAMP was performed by eluting the aluminum oxide columns with 100 mM imidazole (pH 7.4). Both ATP and cAMP fractions were counted for radioactivity using liquid scintillation counting and conversion ratios were calculated as:

$$v=[cAMP]*100\%/([ATP]+[cAMP]).$$

Concentration-response relationships were constructed by plotting cAMP conversion against compound concentration and $IC_{50}$ values were calculated by four-parameter logistic regression. Antagonist potencies ($pA_2$) values were calculated using:

$$pA_2=IC_{50}/(1+[SP]/EC_{50})$$

in which the $IC_{50}$ of the test compound was obtained from concentration-effect relationships, [SP] is the concentration of substance P (in mol/l; typically 10 nM), and the $EC_{50}$ is the potency of substance P at human cloned $NK_1$ receptors.

$NK_1$ Agonist-induced Gerbil Foot-Tapping

The ability of $NK_1$ antagonists to antagonise foot-tapping induced by centrally administered $NK_1$ agonists has been demonstrated (Rupniak and Williams, 1994 (Eur. J. Pharmacol. 265:179); Bristow and Young, 1994 (Eur. J. Pharmacol. 254: 245)). Therefore, we have used this model to assess the in vivo activity of the compounds of the invention.

60 min prior to anaesthesia with $N_2O$ (0.8 L/min), halothane (3%) and $O_2$ (0.8 L/min) male gerbils (40–60 g; Charles River) received an injection of vehicle or test compound (p.o.). Upon successful narcosis the anaesthetic was adjusted to $N_2O$ (0.6 L/min), halothane (1.5%) and $O_2$ (0.6 L/min) and a midline scalp incision made. GR 73632 was infused into the cerebroventricular space (AP—0.5mm, L—1.2 mm, and vertical—4.5 mm from bregma). Following recovery from anaesthesia (about 3–4 min) the foot tapping response was recorded for 5 minutes. The predefined criterion for antagonism of this response was defined as inhibition of foot tapping for $\geq$5 min.

The compounds of the invention have a high affinity for $NK_1$ receptors with $pK_i$-values $\geq$7.0 in the binding assay described above. The compounds of the invention are also active in the cAMP assay, their $pA_2$-values being in line with their $pK_i$-values. Some of the compounds belonging to the invention penetrate the blood brain barrier as is evident from their activity in the neurokinin-agonist induced gerbil foot tapping assay. This property makes them useful in the treatment of CNS disorders.

The invention is further illustrated by means of the following specific examples.

EXAMPLE 1

See Scheme 1

Step 1: To a mixture of trans-pyrrolidine-2,5-dicarboxylic acid diethyl ester hydrochloride (4.2 g) and $N^\alpha$-carbobenzyloxy-D-tryptophan (10.0 g) in acetonitrile (200 mL) was added 1,3-diisopropylcarbodiimide (2.6 mL) and subsequently 4-dimethylaminopyridine (~20 mg). The resulting mixture was stirred overnight at room temperature, then diisopropylethylamine (2.5 mL) was added and stirring was continued for another day. The reaction was quenched with NaOH (aq, 2N) and extracted with ethyl acetate. The organic layer was dried ($Na_2SO_4$), filtered, and concentrated in vacuo. The residue was purified by flash chromatography ($SiO_2$, MTBE) to afford a mixture of (2R,5R,2'R) and (2S,5S,2'R) 1-[2-benzyloxycarbonyl-amino-3-(1H-indol-3-yl)propionyl]-pyrrolidine-2,5-dicarboxylic acid diethyl ester (8.25 g, 90%). $R_f$ 0.62 (EtOAc) (Intermediates 1 and 2).

Step 2: A mixture of (2R,5R,2'R) and (2S,5S,2'R) 1-[2-benzyloxycarbonylamino-3-(1H-indol-3-yl)-propionyl]-pyrrolidine-2,5-dicarboxylic acid diethyl ester (8.5 g), palladium on carbon (10%, ~250 mg), and ethanol (250 mL) was hydrogenated with $H_2$ (1 atm.) overnight. The catalyst was removed by filtration over Celite and the remaining solution was concentrated in vacuo. The resulting two diastereomers could be separated by flash chromatography ($SiO_2$, $CH_2Cl_2$/MeOH/$NH_4OH$ 95:4.5:0.5) to afford (3R,6S,8aS)-3-(1H-Indol-3-ylmethyl)-1,4-dioxo-octahydro-pyrrolo[1,2-a]pyrazine-6-carboxylic acid ethyl ester (2.3 g) and (3R,6R,8aR)-3-(1H-Indol-3-ylmethyl)-1,4-dioxo-octahydro-pyrrolo[1,2-a]pyrazine-6-carboxylic acid ethyl ester (1.75 g) (Intermediates 3 and 4).

Step 3: To a suspension of lithium aluminium hydride (1.2 g) in THF (50 mL) was added a solution of (3R,6R,8aR)-3-(1H-Indol-3-ylmethyl)-1,4-dioxo-octahydro-pyrrolo[1,2-a]pyrazine-6-carboxylic acid ethyl ester (1.75 g) in THF (50 mL). The resulting mixture was heated under reflux for 3 hours, then a mixture of water (3 mL) and THF (30 mL) was added drop-wise followed by 50% sodium hydroxide (aq, 0.5 mL), and heating under reflux was continued for 2 hours. After cooling to room temperature diisopropylethylamine (4 mL) and 3,5-bis(trifluoromethyl)benzoyl chloride (2.4 mL) were added and stirring was continued overnight. Ethyl acetate was added and the mixture extracted with sodium bicarbonate (5% aq. soln.). The organic layer was dried ($Na_2SO_4$), filtered, and concentrated in vacuo. The residue was purified by flash chromatography ($SiO_2$, $CH_2Cl_2$/MeOH/$NH_4OH$ 95:4.5:0.5) to afford 3,5-bis(trifluoromethyl)phenyl-[(3R,6R,8aR)-6-hydroxymethyl-3-(1H-indol- 3-ylmethyl)-hexahydropyrrolo[1,2-a]pyrazin-2-yl]-methanone (1.49 g). MH+ 526; $R_f$ 0.20 (EtOAc) (compound 1).

Step 4: A mixture of (3,5-bis(trifluoromethyl)phenyl)-[(3R,6R,8aR)-6-hydroxymethyl-3-(1H-indol-3-ylmethyl)-hexahydropyrrolo[1,2-a]pyrazin-2-yl]-methanone (1.30 g), triphenylphosphine (1.2 g), carbontetrachloride (4 mL), and acetonitrile (40 mL) was heated at 70° C. for 6 hours. After cooling to room temperature the solvent was removed in vacuo. The residue was purified by ion-exchange chromatography on a strong cation exchange (SCX) column, to afford 3,5-bis(trifluoromethyl)phenyl-[(3R,6R,8aR)-6-chloromethyl-3-(1H-indol-3-ylmethyl)-hexahydropyrrolo[1,2-a]pyrazin-2-yl]-methanone (1.06 g) (Intermediate 5).

Step 5: To a solution of (3,5-bis(trifluoromethyl)phenyl)-[(3R,6R,8aR)-6-chloromethyl-3-(1H-indol-3-ylmethyl)-hexahydropyrrolo[1,2-a]pyrazin-2-yl]-methanone (1.06 g) in dimethylformamide (15 mL) was added morpholine (5 mL). The resulting mixture was heated at 120° C. for 6 hours. After cooling to room temperature, ethyl acetate and 5% aqueous sodiumbicarbonate were added and the layers were separated. The organic layer was dried and concentrated in vacuo. The residue was purified by flash chromatography ($SiO_2$, MTBE/MeOH/$NH_4OH$ 95:4.5:0.5) to afford 3,5-bis(trifluoromethyl)phenyl-[(3R,6R,8aR)-3-(1H-indol-3-ylmethyl)-6-(morpholin-4-ylmethyl)-hexahydropyrrolo[1,2-a]pyrazin-2-yl]-methanone (407 mg). $R_f$ 0.46 (MTBE/MeOH/$NH_4OH$ 95:4.5:0.5) (compound 2).

In a similar manner the following compounds were obtained:

Compound 3; MH+ 595, $R_f$ 0.71 ($CH_2Cl_2$/MeOH/$NH_4OH$ 90:10:1).

Compound 4; $R_f$ 0.38 ($CH_2Cl_2$/MeOH/$NH_4OH$ 90:10:1).

EXAMPLE 2

See Scheme 2

Step 1: To a mixture of $N^\alpha$-9-fluorenylmethoxycarbonyl-L-trans-4-hydroxyproline (10.2 g), D-tryptophan methyl ester hydrochloride (8.1 g), and benzotriazol-1-yloxy-tris(pyrrolidino)-phosphonium hexafluorophosphate (15 g) in acetonitrile (200 mL) was added diisopropylethylamine (15 mL), at 0° C. The resulting mixture was stirred overnight at room temperature. The solvent was removed in vacuo, dissolved in ethyl acetate and extracted twice with water and twice with 2 M hydrochloric acid. The organic layer was dried ($Na_2SO_4$), filtered, and concentrated in vacuo. The residue was dissolved in acetonitrile (200 mL) and piperidine (25 mL) was added, after 2 hours at room temperature the formed 1-(9H-Fluoren-9-ylmethyl)-piperidine was removed by filtration and the remaining solution was left for 72 hours. The formed crystalline material was collected by filtration to afford (3R,7R,8aS)-7-hydroxy-3-(1H-indol-3-ylmethyl)-hexahydro-pyrrolo[1,2-a]pyrazine-1,4-dione (7.4 g) (intermediate 6).

Step 2: To a solution of (3R,7R,8aS)-7-hydroxy-3-(1H-indol-3-ylmethyl)-hexahydropyrrolo[1,2-a]pyrazine-1,4-dione (2.5 g) in dimethylformamide (30 mL) was added imidazole (1.7 g) and tert-butyl-chloro-diphenylsilane (4.35 mL). The resulting mixture was stirred overnight at room temperature and then partitioned between water and ethyl acetate. The organic layer was dried, filtered and concentrated in vacuo. The residue was purified by flash chromatography ($SiO_2$, EtOAc) to afford (3R,7R,8aS)-7-(tert-butyl-diphenylsilanyloxy)-3-(1H-indol-3-ylmethyl)-hexahydropyrrolo[1,2-a]pyrazine-1,4-dione (4.6 g, 99%) (intermediate 7).

Step 3: To a suspension of lithium aluminium hydride (1.8 g) in THF (120 mL) was added a solution of (3R,7R,8aS)-7-(tert-butyl-diphenylsilanyloxy)-3-(1H-indol-3-ylmethyl)-hexahydropyrrolo[1,2-a]pyrazine-1,4-dione (4.6 g) in THF (35 mL). The resulting mixture was heated under reflux overnight, then a mixture of water (1.8 mL) and THF (30 mL) was added dropwise followed by aqueous sodium hydroxide (2 M, 2×1.8 mL). The formed salts were removed by filtration and the remaining solution was concentrated in vacuo. The residue was suspended in ethyl acetate (100 mL) and THF (20 mL), diisopropylethylamine (5 mL) and 3,5-bis(trifluoromethyl)benzoyl chloride (2 mL) were added and the mixture stirred at room temperature overnight. The mixture was extracted with water, dried, filtered and concentrated in vacuo. The residue was purified by flash chromatography ($SiO_2$, MTBE/hexanes 2:1) to afford 3,5-bis(trifluoromethyl)benzoic acid (3R,7R,8aS)-2-(3,5-bis(trifluoromethyl)benzoyl)-3-(1H-indol-3-ylmethyl)-octahydro-pyrrolo[1,2-a]pyrazin-7-yl ester (4.2 g, 65%). MH+ 752 (intermediate 8).

Step 4: A mixture of 3,5-bis(trifluoromethyl)benzoic acid (3R,7R,8aS)-2-(3,5-bis(trifluoromethyl)benzoyl)-3-(1H-indol-3-ylmethyl)-octahydropyrrolo[1,2-a]pyrazin-7-yl ester (4.2 g), 1,4-dioxane (45 mL), methanol (12 ml) and 4M sodium hydroxide (aq, 3 mL) was stirred for 30 min at room temperature. The mixture was concentrated and the residue partitioned between water and ethyl acetate. The organic layer was dried, filtered and concentrated to afford 3,5-bis(trifluoromethyl)phenyl-[(3R,7R,8aS)-7-hydroxy-3-(1H-indol-3-ylmethyl)hexahydropyrrolo[1,2-a]pyrazin-2-yl]-methanone (4 g) (compound 5).

Step 5a: To a solution of 3,5-bis(trifluoromethyl)phenyl-[(3R,7R,8aS)-7-hydroxy-3-(1H-indol-3-ylmethyl)hexahydropyrrolo[1,2-a]pyrazin-2-yl]-methanone (0.54 g) in ethyl acetate (20 mL) was added diisopropylethylamine (2 mL) and methanesulfonyl chloride (0.2 mL). The resulting mixture was stirred overnight at room temperature and concentrated in vacuo. To the residue was added morpholine (4 mL) and the mixture was heated at 95° C. for 4 hours. The excess morpholine was removed in vacuo and the residue purified by preparative HPLC to afford 3,5-bis(trifluoromethyl)phenyl-[(3R,7S,8aS)-3-(1H-indol-3-ylmethyl)-7-(morpholin-4-yl)-hexahydro-pyrrolo[1,2-a]pyrazin-2-yl]-methanone (81 mg). MH+ 581 (compound 6).

Step 5b: To a solution of 3,5-bis(trifluoromethyl)phenyl-[(3R,7R,8aS)-7-hydroxy-3-(1H-indol-3-ylmethyl)hexahydropyrrolo[1,2-a]pyrazin-2-yl]-methanone (0.68 g) in dimethyl formamide (20 mL) was added diisopropylethylamine (2 mL) and methanesulfonyl chloride (0.2 mL). The resulting mixture was stirred 1 hour at room temperature then cesium bromide (excess) was added and the mixture stirred for 5 hours at 95° C. The intermediate bromide was isolated by partitioning between water and ethyl acetate, concentration of the organic layer and purification by chromatography. To the bromide was added morpholine (4 mL) and the mixture was heated at 95° C. for 4 hours. The excess morpholine was removed in vacuo and the residue purified by preparative HPLC to afford 3,5-bis(trifluoromethyl)phenyl-[(3R,7R,8aS)-3-(1H-indol-3-ylmethyl)-7-(morpholin-4-yl)-hexahydro-pyrrolo[1,2-a]-pyrazin-2-yl]-methanone (101 mg). MH+ 581 (compound 7).

In a similar manner the compounds 8 and 9 were obtained.

EXAMPLE 3

See Scheme 3

Step 1: To a solution of 5-oxo-piperidine-1,2-dicarboxylic acid 1-benzyl ester (93.5 g) in acetonitrile (1 L) was added a solution of diisopropylcarbodiimide (53 mL) in acetonitrile (50 mL) and the mixture was cooled to 5° C. To the resulting suspension was added portion-wise D-tryptophan methyl ester hydrochloride (85.5 g) and drop-wise a solution of diisopropylethylamine (58.6 mL) in acetonitrile (50 mL). The resulting mixture was stirred 18 hours at room temperature then filtered and concentrated in vacuo. The residue was dissolved in dichloromethane washed with hydrochloric acid (1 M) twice and water twice, dried, filtered and concentrated in vacuo to afford a mixture of (2R,2'R)- and (2S,2'R)-2-[2-(1H-Indol-3-yl)-1-methoxycarbonyl-ethylcarbamoyl]-5-oxo-piperidine-1-carboxylic acid benzyl ester (171.2 9) (intermediates 9 and 10) which was used as such in the next step.

Step 2: A mixture of (2R,2'R)- and (2S,2'R)-2-[2-(1H-Indol-3-yl)-1-methoxycarbonyl-ethylcarbamoyl]-5-oxo-piperidine-1-carboxylic acid benzyl ester (138.9 g), oxalic acid (180 g) and 1,3-propanediol (87 mL) in acetonitrile (1.5 L) was heated at 40° C. for 20 hours. Subsequently the solvent was removed in vacuo and the residue purified by flash chromatography ($SiO_2$, $CH_2Cl_2$/MeOH 99:1) to afford a mixture of (9R,2'R)- and (9S,2'R)-9-[2-(1H-Indol-3-yl)-1-methoxycarbonyl-ethylcarbamoyl]-1,5-dioxa-8-aza-spiro[5.5]undecane-8-carboxylic acid benzyl ester (118 g). $MH^+$ 536, $R_f$ 0.07 ($CH_2Cl_2$/MeOH 99:1) (intermediates 11 and 12).

Step 3: To a solution of a mixture of (9R,2'R)- and (9S,2'R) 9-[2-(1H-Indol-3-yl)-1-methoxycarbonyl-ethylcarbamoyl]-1,5-dioxa-8-aza-spiro[5.5]undecane-8-carboxylic acid benzyl ester (92.8 g) in methanol (1 L) was added 10% palladium on carbon (~5 g). The resulting mixture was hydrogenated with $H_2$ (1 atm.) overnight at room temperature. The catalyst was removed by filtration over Celite and the remaining solution was concentrated in vacuo to afford a mixture of (2R,9'R) and (2R,9'S)-2-[(1,5-Dioxa-8-aza-spiro[5.5]undecane-9-carbonyl)-amino]-3-(1H-indol-3-yl)-propionic acid methyl ester (69.0 g). $R_f$ 0.24 ($CH_2Cl_2$/MeOH/$NH_4OH$ 92:7.5:0.5) (intermediates 13 and 14).

Step 4: A mixture of (2R,9'R) and (2R,9'S)-2-[(1,5-Dioxa-8-aza-spiro[5.5]undecane-9-carbonyl)-amino]-3-(1H-indol-3-yl)-propionic acid methyl ester (69.0 g) and acetic acid (9 mL) in acetonitrile (900 mL) was heated under reflux overnight. After cooling to room temperature the mixture was concentrated to approximately one third its original volume. The formed precipitate was collected by filtration to afford (3R,9aS)-3-(1H-indol-3-ylmethyl)-hexahydro-spiro [2H-pyrido[1,2-a]pyrazine-1,4-dione-7,2'-[1,3]dioxane] (23.7 g; $R_f$ 0.34 ($Et_2O$/MeOH 9:1)). Concentration of the filtrate and purification of the residue by flash chromatography ($SiO_2$, $Et_2O$/MeOH 9:1) afforded (3R,9aR)-3-(1H-indol-3-ylmethyl)-hexahydro-spiro[2H-pyrido[1,2-a]pyrazine-1,4-dione-7,2'-[1,3]dioxane] (20.6 g; $R_f$ 0.18 ($Et_2O$/MeOH 9:1) (intermediate 15).

Step 5: To a suspension of lithium aluminium hydride (10.6 g) in THF (500 mL) was added drop-wise a solution of (3R,9aR)-3-(1H-indol-3-ylmethyl)-hexahydro-spiro[2H-pyrido[1,2-a]pyrazine-1,4-dione-7,2'-[1,3]dioxane] (20.6 g) in THF (100 mL), and the resulting mixture was heated under reflux for 2 days. After cooling to 5° C. water (9.2 mL) 2M sodium hydroxide (aq, 18.4 mL), and again water (9.2 mL) were added drop-wise. The resulting mixture was heated under reflux for another hour, cooled to room temperature, filtered over Celite, and concentrated in vacuo to afford crude (3R,9aR)-3-(1H-indol-3-ylmethyl)-octahydro-spiro[2H-pyrido[1,2-a]pyrazine-7,2'-[1,3]dioxane] (19.7 g, $R_f$ 0.16 ($CH_2Cl_2$/MeOH/$NH_4OH$ 92:7.5:0.5)) (intermediate 16) which was used as such in the next step.

Step 6: To a solution of (3R,9aR)-3-(1H-indol-3-ylmethyl)-octahydro-spiro[2H-pyrido[1,2-a]pyrazine-7,2'-[1,3]dioxane] (19.7 g) in dichloromethane was added diisopropylethylamine (9.6 mL) at room temperature and at 5° C., 3,5-bis(trifluoromethyl)benzoyl chloride (10 mL) drop-wise. The resulting mixture was stirred at room temperature overnight, concentrated in vacuo and purified by column chromatography ($SiO_2$, $CH_2Cl_2$/MeOH/$NH_4OH$ 96:3.75:0.25) to afford (3R,9aR)-2-[3,5-bis(trifluoromethyl)benzoyl]-3-(1H-indol-3-ylmethyl)-octahydro-spiro-[2H-pyrido[1,2-a]pyrazine-7,2'-[1,3]dioxane] (30.0 g). $R_f$ 0.35 ($CH_2Cl_2$/MeOH/$NH_4OH$ 96:3.75:0.25) (compound 10).

Step 7: A mixture of (3R,9aR)-2-[3,5-bis(trifluoromethyl)benzoyl]-3-(1H-indol-3-ylmethyl)-octahydro-spiro-[2H-pyrido[1,2-a]pyrazine-7,2'-[1,3]dioxane] (30.0 g) in acetic acid (150 mL) and 6M hydrochloric acid (150 mL) was heated at 40° C. for three days. After cooling to room temperature dichloromethane (750 mL) and 2M sodium hydroxide (aq., 1700 mL) were added. The layers were separated and the aqueous layer was extracted twice with dichloromethane. The combined organic layers were washed with water, concentrated in vacuo, and purified by flash-chromatography ($SiO_2$, $CH_2Cl_2$/MeOH 98:2) to afford (3R,9aR)-2-[3,5-bis(trifluoromethyl)benzoyl]-3-(1H-indol-3-ylmethyl)-octahydro-2H-pyrido[1,2-a]pyrazin-7-one (21.7 g). $R_f$ 0.12 ($CH_2Cl_2$/MeOH 98:2) (compound 11).

Step 8: To a suspension of (3R,9aR)-2-[3,5-bis(trifluoromethyl)benzoyl]-3-(1H-indol-3-ylmethyl)-octahydro-2H-pyrido[1,2-a]pyrazin-7-one (5.6 g) in acetic acid (75 mL) was added sodium triacetoxyborohydride (6.78 g). The resulting mixture was stirred for one hour at room temperature then poured in water and basified with 2M sodium hydroxide (aq.). The formed precipitate was collected by filtration, washed with water, suspended in toluene and concentrated in vacuo to afford 3,5-bis(trifluoromethyl) phenyl-[(3R,7S,9aR)-7-hydroxy-3-(1H-indol-3-ylmethyl)-octahydropyrido[1,2-a]pyrazin-2-yl]-methanone (5.7 g). $R_f$ 0.35 ($CH_2Cl_2$/MeOH 9:1) (compound 12).

Step 9: To a suspension of 3,5-bis(trifluoromethyl)phenyl-[(3R,7S,9aR)-7-hydroxy-3-(1H-indol-3-ylmethyl)-octahydropyrido[1,2-a]pyrazin-2-yl]-methanone (3.85 g) in acetonitrile was added carbon tetrabromide (11.6 g) and triphenylphosphine (9.18 g), the resulting mixture was stirred at room temperature overnight. The formed precipitate was removed by filtration and the filtrate was concentrated in vacuo. The residue was purified by flash-chromatography ($SiO_2$, $CH_2Cl_2$/MeOH 98:2) to afford 3,5-bis (trifluoromethyl)phenyl-[(3R,9aR)-7-bromo-3-(1H-indol-3-ylmethyl)-octahydropyrido[1,2-a]pyrazin-2-yl]-methanone (3.5 g). MH+ 588, $R_f$ 0.38 (CH$_2$Cl$_2$/MeOH 97:3) (intermediate 17).

Step 10: A mixture of 3,5-bis(trifluoromethyl)phenyl-[(3R,9aR)-7-bromo-3-(1H-indol-3-ylmethyl)-octahydropyrido[1,2-a]pyrazin-2-yl]-methanone (2.94 g) and morpholine (0.92 mL) in acetonitrile (100 mL) was heated at 80° C. for 40 hours. After cooling to room temperature the mixture was concentrated in vacuo and the residue purified by flash-chromatography (SiO$_2$, CH$_2$Cl$_2$/MeOH/NH$_4$OH 980: 18.75:1.25) to afford 3,5-bis(trifluoromethyl)phenyl-[(3R,7R,9aR)-3-(1H-indol-3-ylmethyl)-7-morpholin-4-yl-octahydropyrido[1,2-a]pyrazin-2-yl]-methanone (1.6 g, $R_f$ 0.33 (CH$_2$Cl$_2$/MeOH/NH$_4$OH 92:7.5:0.5)) (compound 13) and 3,5-bis(trifluoromethyl)phenyl-[(3R,7S,9aR)-3-(1H-indol-3-ylmethyl)-7-morpholin-4-yl-octahydropyrido[1,2-a]pyrazin-2-yl]-methanone (1.28 g, $R_f$ 0.27 (CH$_2$Cl$_2$/MeOH/NH$_4$OH 92:7.5:0.5)) (compound 14).

In a similar manner the compounds 15–23 and 33–40 were obtained.

EXAMPLE 4

See Scheme 3

A mixture of (3R,9aR)-2-[3,5-bis(trifluoromethyl)benzoyl]-3-(1H-indol-3-ylmethyl)-octahydro-2H-pyrido[1,2-a]pyrazin-7-one (0.785 g, see example 3 steps 1–7), pyrrolidine (0.107 g), acetic acid (0.09 g) and sodium triacetoxyborohydride (0.47 g) in 1,2-dichloroethane (60 mL) was stirred for three days at room temperature. The resulting mixture was poured into water, basified with sodium bicarbonate (5% aq. soln.) and extracted with dichloromethane. The organic layer was concentrated and the residue was purified by column chromatography (SiO$_2$, CH$_2$Cl$_2$/MeOH/NH$_4$OH 92:7.5:0.5) to afford 3,5-bis(trifluoromethyl)phenyl-[(3R,7R,9aR)-3-(1H-indol-3-ylmethyl)-7-pyrrolidin-1-yl-octahydropyrido[1,2-a]pyrazin-2-yl]-methanone (0.20 g, $R_f$ 0.23 (CH$_2$Cl$_2$/MeOH/NH$_4$OH 92:7.5:0.5)) (compound 24) and 3,5-bis(trifluoromethyl)phenyl-[(3R,7S,9aR)-3-(1H-indol-3-ylmethyl)-7-pyrrolidin-1-yl-octahydropyrido[1,2-a]pyrazin-2-yl]-methanone (0.48 g, $R_f$ 0.15 (CH$_2$Cl$_2$/MeOH/NH$_4$OH 92:7.5:0.5)) (compound 25).

In a similar manner the compounds 26–28 were obtained.

EXAMPLE 5

See Scheme 3

Step 1: To a suspension of (3R,7S,9aR)-(3-benzyl-7-hydroxy-octahydropyrido[1,2-a]pyrazin-2-yl)-(3,5-bis(trifluoromethyl)phenyl)-methanone (3.3 g, prepared analogous to example 3 steps 1–8) in dichloromethane (100 mL) was added diisopropylethylamine (2.4 mL) and methanesulfonyl chloride (0.8 mL), at 5° C. The resulting mixture was stirred at room temperature for 15 min. and concentrated in vacuo. The residue was purified by column chromatography (SiO$_2$, CH$_2$Cl$_2$/MeOH 95:5) to afford methanesulfonic acid (3R,7S,9aR)-3-benzyl-2-(3,5-bis(trifluoromethyl)benzoyl)-octahydropyrido[1,2-a]pyrazin-7-yl ester (3.8 g). $R_f$ 0.67 (CH$_2$Cl$_2$/MeOH 95:5) (intermediate 18).

Step 2: A mixture of methanesulfonic acid (3R,7S,9aR)-3-benzyl-2-(3,5-bis(trifluoromethyl)benzoyl)-octahydropyrido[1,2-a]pyrazin-7-yl ester (1.97 g) and morpholine (0.44 mL) in acetonitrile (50 mL) was heated at 80° C. for 40 hours. After cooling to room temperature the mixture was concentrated in vacuo and the residue purified by flash-chromatography (SiO$_2$, CH$_2$Cl$_2$/MeOH/NH$_4$OH 980:18.75: 1.25) to afford 3,5-bis(trifluoromethyl)phenyl-[(3R,7R,9aR)-3-benzyl-7-morpholin-4-yl-octahydropyrido[1,2-a]pyrazin-2-yl]-methanone (0.97 g, $R_f$ 0.24 (CH$_2$Cl$_2$/MeOH/NH$_4$OH 96:3.75:0.25)) (compound 29) and 3,5-bis(trifluoromethyl)phenyl-[(3R,7S,9aR)-3-benzyl-7-morpholin-4-yl-octahydropyrido[1,2-a]pyrazin-2-yl]-methanone (0.75 g, $R_f$ 0.15 (CH$_2$Cl$_2$/MeOH/NH$_4$OH 96:3.75:0.25)) (compound 30).

In a similar manner the following compounds were obtained:
compound 31 and 32,
compound 41; $R_f$ 0.11 (CH$_2$Cl$_2$/MeOH/NH$_4$OH (96:3.75:0.25))
compound 42; $R_f$ 0.06 (CH$_2$Cl$_2$/MeOH/NH$_4$OH (96:3.75:0.25))
compound 43; $R_f$ 0.08 (CH$_2$Cl$_2$/MeOH/NH$_4$OH (96:3.75:0.25))
compound 44; $R_f$ 0.05 (CH$_2$Cl$_2$/MeOH/NH$_4$OH (96:3.75:0.25))
compounds 45, 46, 55, 56, 58 and 59
compound 57; $R_f$ 0.10 (CH$_2$Cl$_2$/MeOH/NH$_4$OH (98:1.85:0.15))

EXAMPLE 6

Ester Pro-drugs

To a solution of (3,5-bis(trifluoromethyl)phenyl)-[(3R,6R,8aR)-6-hydroxymethyl-3-(1H-indol-3-ylmethyl)-hexahydropyrrolo[1,2-a]pyrazin-2-yl]-methanone (0.52 g) in acetonitrile (40 mL) was added diisopropylethylamine (0.17 mL) and a solution of acetyl chloride (0.8 mL) in acetonitrile (10 mL), at room temperature. The resulting mixture was stirred at room temperature overnight, and concentrated in vacuo. The residue was purified by column chromatography (SiO$_2$, CH$_2$Cl$_2$/MeOH 97:3) to afford methanesulfonic acid Acetic acid 2-(3,5-bis(trifluoromethyl)benzoyl)-3-(1H-indol-3-ylmethyl)-hexahydropyrrolo[1,2-a]pyrazin-6-ylmethyl ester (0.32 g). $R_f$ 0.33 (CH$_2$Cl$_2$/MeOH 97:3) (compound 47).

In a similar manner the following compounds were obtained:
Compound 48; $R_f$ 0.50 (CH$_2$Cl$_2$/MeOH 97:3)
Compound 49; $R_f$ 0.51 (CH$_2$Cl$_2$/MeOH 97:3)
Compound 50; $R_f$ 0.50 (CH$_2$Cl$_2$/MeOH 97:3)
Compound 51; $R_f$ 0.12 (CH$_2$Cl$_2$/MeOH 98:2)
Compound 52; $R_f$ 0.47 (CH$_2$Cl$_2$/MeOH 95:5)
Compound 53; $R_f$ 0.21 (CH$_2$Cl$_2$/MeOH 97:3)
Compound 54

The compounds of the invention, as exemplified by the compounds 1–59, have a high affinity for NK1 receptors with pK$_i$-values $\geq 7.0$ in the binding assay described above. As outlined in detail in the examples given, some of these compounds have been used as intermediates in the synthesis of other compounds. The compounds of the invention are active in the cAMP assay, their pA$_2$-values being in line with their pK$_i$-values. Some of the compounds belonging to the invention penetrate the blood brain barrier as is evident from their activity in the neurokinin-agonist induced gerbil foot tapping assay. This property makes them useful in the treatment of CNS disorders.

| Cmp. | X | R1 | R2 | R3 | R4 | R5 | R6 | n | 3 | 6 | 7 | a |
|---|---|---|---|---|---|---|---|---|---|---|---|---|
| 1 | O | 3-Indolyl | 3-CF₃ | 5-CF₃ | | | CH₂OH | 1 | R | R | | R |
| 2 | O | 3-Indolyl | 3-CF₃ | 5-CF₃ | | | CH₂N(CH₂CH₂)₂O | 1 | R | R | | R |
| 3 | O | 3-Indolyl | 3-CF₃ | 5-CF₃ | | | CH₂N(CH₂CH₂)₂O | 1 | R | R | | S |
| 4 | O | 3-Indolyl | 3-CF₃ | 5-CF₃ | | | CH₂N(CH₂CH₂)₂O | 1 | R | S | | R |
| 5 | O | 3-Indolyl | 3-CF₃ | 5-CF₃ | OH | | | 1 | R | | R | S |
| 6 | O | 3-Indolyl | 3-CF₃ | 5-CF₃ | Morpholin-4-yl | | | 1 | R | | S | S |
| 7 | O | 3-Indolyl | 3-CF₃ | 5-CF₃ | Morpholin-4-yl | | | 1 | R | | R | S |
| 8 | O | 3-Indolyl | 3-CF₃ | 5-CF₃ | Morpholin-4-yl | | | 1 | R | | R | R |
| 9 | O | 3-Indolyl | 3-CF₃ | 5-CF₃ | Morpholin-4-yl | | | 1 | R | | S | R |
| 10 | O | 3-Indolyl | 3-CF₃ | 5-CF₃ | OCH₂CH₂CH₂O | | | 2 | R | | | R |
| 11 | O | 3-Indolyl | 3-CF₃ | 5-CF₃ | =O | | | 2 | R | | | R |
| 12 | O | 3-Indolyl | 3-CF₃ | 5-CF₃ | OH | | | 2 | R | | R | R |
| 13 | O | 3-Indolyl | 3-CF₃ | 5-CF₃ | Morpholin-4-yl | | | 2 | R | | R | R |
| 14 | O | 3-Indolyl | 3-CF₃ | 5-CF₃ | Morpholin-4-yl | | | 2 | R | | S | R |
| 15 | O | 3-Indolyl | 3-CF₃ | 5-CF₃ | Morpholin-4-yl | | | 2 | R | | R | S |
| 16 | O | 3-Indolyl | 3-CF₃ | 5-CF₃ | Morpholin-4-yl | | | 2 | R | | S | S |
| 17 | O | 3-Indolyl | 3-CF₃ | 5-CF₃ | Morpholin-4-yl | | | 2 | S | | S | S |
| 18 | O | 3-Indolyl | 3-CF₃ | 5-CF₃ | Morpholin-4-yl | | | 2 | S | | R | S |
| 19 | O | 3-Indolyl | 3-CF₃ | 5-CF₃ | Piperidin-1-yl | | | 2 | R | | R | R |
| 20 | O | 3-Indolyl | 3-CF₃ | 5-CF₃ | Piperidin-1-yl | | | 2 | R | | S | R |
| 21 | O | 3-Indolyl | 3-CF₃ | 5-CF₃ | 2,6-Dimethyl-morpholin-4-yl | | | 2 | R | | R | R |
| 22 | O | 3-Indolyl | 3-CF₃ | 5-CF₃ | 2,6-Dimethyl-morpholin-4-yl | | | 2 | R | | S | R |
| 23 | O | 3-Indolyl | 3-CF₃ | 5-CF₃ | Imidazol-1-yl | | | 2 | R | | S | R |
| 24 | O | 3-Indolyl | 3-CF₃ | 5-CF₃ | Pyrrolidin-1-yl | | | 2 | R | | R | R |
| 25 | O | 3-Indolyl | 3-CF₃ | 5-CF₃ | Pyrrolidin-1-yl | | | 2 | R | | S | R |
| 26 | O | 3-Indolyl | 3-CF₃ | 5-CF₃ | Diethylamino | | | 2 | R | | R | R |
| 27 | O | 3-Indolyl | 3-CF₃ | 5-CF₃ | Diethylamino | | | 2 | R | | S | R |
| 28 | O | 3-Indolyl | 3-CF₃ | 5-CF₃ | Morpholin-4-ylamino | | | 2 | R | | RS | R |
| 29 | O | Phenyl | 3-CF₃ | 5-CF₃ | Morpholin-4-yl | | | 2 | R | | R | R |
| 30 | O | Phenyl | 3-CF₃ | 5-CF₃ | Morpholin-4-yl | | | 2 | R | | S | R |
| 31 | O | Phenyl | 3-CF₃ | 5-CF₃ | Morpholin-4-yl | | | 2 | R | | R | S |
| 32 | O | Phenyl | 3-CF₃ | 5-CF₃ | Morpholin-4-yl | | | 2 | R | | S | S |
| 33 | O | 3-Indolyl | 3-CF₃ | 5-CF₃ | 1,1-Dioxo-thiomorpholin-4-yl | | | 2 | R | | R | R |
| 34 | O | 3-Indolyl | 3-CF₃ | 5-CF₃ | 1,1-Dioxo-thiomorpholin-4-yl | | | 2 | R | | S | R |
| 35 | O | 3-Indolyl | 3-CF₃ | 5-CF₃ | 3-methoxymethyl-morpholin-4-yl | | | 2 | R | | RS | R |
| 36 | O | 3-Indolyl | 3-CF₃ | 5-CF₃ | 3,5-bis(methoxymethyl)-morpholin-4-yl | | | 2 | R | | S | R |
| 37 | O | 3-Indolyl | 3-CF₃ | 5-CF₃ | 3,5-bis(methoxymethyl)-morpholin-4-yl | | | 2 | R | | R | R |
| 38 | O | 3-Indolyl | 3-CF₃ | 5-CF₃ | 3-oxa-8-azabicyclo[3.2.1]oct-8-yl | | | 2 | R | | RS | R |
| 39 | O | 3-Indolyl | 3-CF₃ | 5-CF₃ | trans-3,5-dimethyl-morpholin-4-yl | | | 2 | R | | RS | R |
| 40 | O | 3-Indolyl | 3-CF₃ | 5-CF₃ | cis-3,5-dimethyl-morpholin-4-yl | | | 2 | R | | RS | R |
| 41 | O | 3-Indolyl | 3-Cl | 5-Cl | Morpholin-4-yl | | | 2 | R | | R | R |
| 42 | O | 3-Indolyl | 3-Cl | 5-Cl | Morpholin-4-yl | | | 2 | R | | S | R |
| 43 | O | 3-Indolyl | 3-CH₃ | 5-CH₃ | Morpholin-4-yl | | | 2 | R | | R | R |
| 44 | O | 3-Indolyl | 3-CH₃ | 5-CH₃ | Morpholin-4-yl | | | 2 | R | | S | R |
| 45 | O | 3-Indolyl | 3-CF₃ | 5-F | Morpholin-4-yl | | | 2 | R | | R | R |
| 46 | O | 3-Indolyl | 3-CF₃ | 5-F | Morpholin-4-yl | | | 2 | R | | S | R |
| 47 | O | 3-Indolyl | 3-CF₃ | 5-CF₃ | | | CH₂OCOCH₃ | 1 | R | R | | R |
| 48 | O | 3-Indolyl | 3-CF₃ | 5-CF₃ | | | CH₂OCOC(CH₃)₃ | 1 | R | R | | R |
| 49 | O | 3-Indolyl | 3-CF₃ | 5-CF₃ | | | CH₂OCO(CH₂)₅CH₃ | 1 | R | R | | R |
| 50 | O | 3-Indolyl | 3-CF₃ | 5-CF₃ | | | CH₂OCO(CH₂)₈CH₃ | 1 | R | R | | R |
| 51 | O | 3-Indolyl | 3-CF₃ | 5-CF₃ | | | CH₂OCO(CH₂)₂CH₃ | 1 | R | R | | R |
| 52 | O | 3-Indolyl | 3-CF₃ | 5-CF₃ | | | CH₂OCOCH₂OCOCH₃ | 1 | R | R | | R |
| 53 | O | 3-Indolyl | 3-CF₃ | 5-CF₃ | | | CH₂OH nicotinic acid ester | 1 | R | R | | R |
| 54 | O | 3-Indolyl | 3-CF₃ | 5-CF₃ | | | CH₂OCOCH₂N(CH₃)₂ | 1 | R | R | | R |
| 55 | O | 4-Fluorophenyl | 3-CF₃ | 5-CF₃ | Morpholin-4-yl | | | 2 | R | | R | R |
| 56 | O | 4-Fluorophenyl | 3-CF₃ | 5-CF₃ | Morpholin-4-yl | | | 2 | R | | S | R |
| 57 | O | 3-Indolyl | 2-CF₃ | 5-CF₃ | Morpholin-4-yl | | | 2 | R | | S | |
| 58 | O | Benzo[b]thiophen-3-yl | 3-CF₃ | 5-CF₃ | Morpholin-4-yl | | | 2 | R | | R | R |
| 59 | O | Benzo[b]thiophen-3-yl | 3-CF₃ | 5-CF₃ | Morpholin-4-yl | | | 2 | R | | S | R |

What is claimed is:

1. Compounds of the formula (1):

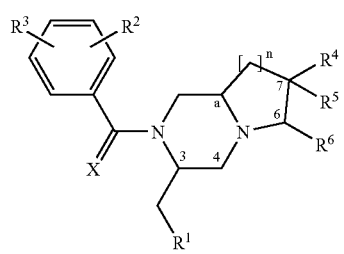

wherein:
R¹ represents phenyl, 2-indolyl, 3-indolyl, 3-indazolyl or benz[b]thiophen-3-yl, which groups may be substituted with halogen or alkyl (1–3C),
R² and R³ independently represent halogen, H, OCH₃, CH₃ or CF₃,
R⁴, R⁵ and R⁶ independently represent H, OH, O-alkyl (1–4C), CH₂OH, NH₂, dialkyl(1–3C)N, pyrrolidin-1-yl, piperidin-1-yl, morpholin-4-yl or morpholin-4-yl substituted with one or two methyl or methoxymethyl groups, morpholin-4-ylamino, morpholin-4-ylmethyl, imidazol-1-yl, thiomorpholin-4-yl, 1,1-dioxothiomorpholin-4-yl or 3-oxa-8-azabicyclo[3.2.1]oct-8-yl; or R⁴ and R⁵ together represent a keto, a 1,3-dioxan-2-yl or a 1,3-dioxolan-2-yl group,
X represents either O or S,
n has the value of 1, 2 or 3,
a is the asymmetrical carbon atom 8a, 9a or 10a when n equals 1, 2 or 3 respectively,
pharmacologically acceptable salts thereof, and including all possible stereo-isomers in which the substituents on the asymmetrical carbon atoms 3 and 'a', as well as on the potentially asymmetrical carbon atoms 6 and 7, are in either the R-configuration or the S-configuration, as well as esters thereof.

2. Compounds as claimed in claim 1 wherein R¹ is 3-indolyl, R² and R³ are CF₃ groups in the 3 and 5 positions, X represents O, and n has the value of either 1 or 2.

3. Compounds as claimed in claim 2 wherein R⁵ is hydrogen and which stereochemistry is 3R.

4. Compounds having the formula (4):

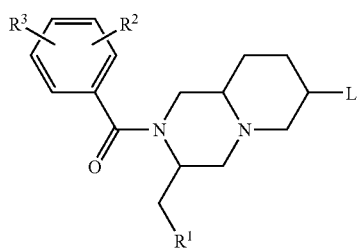

wherein:
R¹ represents phenyl, 2-indolyl, 3-indolyl, 3-indazolyl or benz[b]thiophen-3-yl, which groups are optionally substituted with halogen or alkyl (1–3C),
R² and R³ independently represent halogen, H, OCH₃, CH₃ or CF₃, and L represents a leaving group, selected from chloro, bromo and methanesulfonate, wherein said compounds are useful in the synthesis of compounds having formula (1):

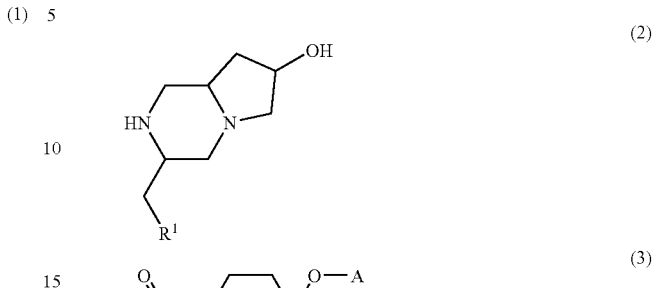

wherein:
R¹, R², and R³ have the meanings given above,
R⁴, R⁵ and R⁶ independently represent H, OH, O-alkyl (1–4C), CH₂OH, NH₂, dialkyl(1–3C)N, pyrrolidin-1-yl, piperidin-1-yl, morpholin-4-yl or morpholin-4-yl substituted with one or two methyl or methoxymethyl groups, morpholin-4-ylamino, morpholin-4-ylmethyl, imidazol-1-yl, thiomorpholin-4-yl, 1,1-dioxothiomorpholin-4-yl or 3-oxa-8-azabicyclo[3.2.1]oct-8-yl; or R⁴ and R⁵ together represent a keto, a 1,3-dioxan-2-yl or a 1,3-dioxolan-2-yl group,
X represents either O or S,
n has the value of 1, 2 or 3,
a is the asymmetrical carbon atom 8a, 9a or 10a when n equals 1, 2 or 3 respectively,
pharmacologically acceptable salts thereof, and including all possible stereo-isomers in which the substituents on the asymmetrical carbon atoms 3 and 'a', as well as on the potentially asymmetrical carbon atoms 6 and 7, are in either the R-configuration or the S-configuration, as well as esters thereof.

5. A pharmaceutical composition comprising a pharmaceutically acceptable carrier and/or at least one pharmaceutically acceptable auxiliary substance, and a pharmacologically active amount of at least one compound of formula (1) as claimed in claim 1 as an active ingredient.

6. A method for the treatment of at least one disease, comprising administration of a composition comprising a pharmaceutically acceptable amount of at least one compound of claim 1, wherein said disease is chosen from acute and chronic pain, emesis, asthma, unipolar depressive disorders, minor depression, seasonal affective disorder, postnatal depression, dysthymia, major depression, and anxiety.

* * * * *

UNITED STATES PATENT AND TRADEMARK OFFICE
CERTIFICATE OF CORRECTION

PATENT NO. : 7,202,238 B2  Page 1 of 1
APPLICATION NO. : 10/490364
DATED : April 10, 2007
INVENTOR(S) : de Boer et al.

It is certified that error appears in the above-identified patent and that said Letters Patent is hereby corrected as shown below:

On The Title Page,
Item (86), file date, "Mar. 22, 2004" should read --Mar. 23, 2004--.

Col. 20, lines 5-33, delete the formulas: 2, 3, and 4.

Col. 20, lines 5-33, insert formula 1, --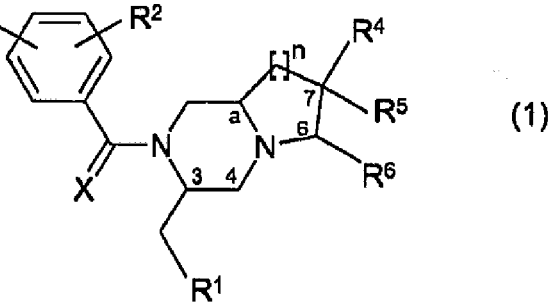 (1)

--

Signed and Sealed this

Thirty-first Day of July, 2007

JON W. DUDAS
*Director of the United States Patent and Trademark Office*